US008467495B2

(12) United States Patent
Okada et al.

(10) Patent No.: US 8,467,495 B2
(45) Date of Patent: Jun. 18, 2013

(54) RADIOGRAPHIC IMAGE CAPTURING APPARATUS AND RADIOGRAPHIC IMAGE CAPTURING METHOD

(75) Inventors: Naoyuki Okada, Kanagawa-ken (JP); Hajime Nakata, Kanagawa-ken (JP); Hiroki Nakayama, Kanagawa-ken (JP); Takao Yoshida, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 291 days.

(21) Appl. No.: 12/923,556

(22) Filed: Sep. 28, 2010

(65) Prior Publication Data
US 2011/0075799 A1 Mar. 31, 2011

(30) Foreign Application Priority Data

Sep. 29, 2009 (JP) ................................. 2009-224505

(51) Int. Cl.
*A61B 6/02* (2006.01)
*G21K 1/04* (2006.01)
(52) U.S. Cl.
USPC ................ 378/41; 378/37; 378/151; 378/206
(58) Field of Classification Search
USPC ................................. 378/37, 41, 65, 151, 206
See application file for complete search history.

(56) References Cited

U.S. PATENT DOCUMENTS

| 5,539,797 | A | * | 7/1996 | Heidsieck et al. | 378/37 |
|---|---|---|---|---|---|
| 5,594,769 | A | * | 1/1997 | Pellegrino et al. | 378/37 |
| 5,627,869 | A | * | 5/1997 | Andrew et al. | 378/37 |
| 5,964,715 | A | * | 10/1999 | Thunberg | 600/562 |
| 6,118,848 | A | * | 9/2000 | Reiffel | 378/65 |
| 6,125,164 | A | * | 9/2000 | Murphy et al. | 378/65 |
| 6,307,914 | B1 | * | 10/2001 | Kunieda et al. | 378/65 |
| 6,516,046 | B1 | * | 2/2003 | Frohlich et al. | 378/65 |
| 6,647,092 | B2 | * | 11/2003 | Eberhard et al. | 378/65 |
| 6,888,919 | B2 | * | 5/2005 | Graf | 378/65 |
| 6,914,959 | B2 | * | 7/2005 | Bailey et al. | 378/65 |
| 6,990,175 | B2 | * | 1/2006 | Nakashima et al. | 378/65 |
| 7,050,544 | B2 | * | 5/2006 | Karlsson et al. | 378/158 |
| 7,120,231 | B2 | * | 10/2006 | Spahn | 378/151 |
| 7,133,492 | B2 | * | 11/2006 | Kramp et al. | 378/62 |
| 7,204,640 | B2 | * | 4/2007 | Fu et al. | 378/65 |
| 7,206,374 | B2 | * | 4/2007 | Zetterlund | 378/37 |
| 7,221,733 | B1 | * | 5/2007 | Takai et al. | 378/65 |
| 7,227,925 | B1 | * | 6/2007 | Mansfield et al. | 378/65 |
| 7,239,684 | B2 | * | 7/2007 | Hara et al. | 378/65 |
| 7,453,984 | B2 | * | 11/2008 | Chen et al. | 378/65 |
| 7,526,065 | B2 | * | 4/2009 | Hardesty | 378/62 |
| 8,184,770 | B2 | * | 5/2012 | Fischer et al. | 378/62 |

FOREIGN PATENT DOCUMENTS

| JP | 54-032458 | 10/1979 |
|---|---|---|
| JP | 08-107891 | 4/1996 |

* cited by examiner

*Primary Examiner* — Allen C. Ho
(74) *Attorney, Agent, or Firm* — Jean C. Edwards, Esq.; Edwards Neils PLLC

(57) ABSTRACT

In a radiographic image capturing apparatus, a biopsy region positional information calculator calculates a three-dimensional position of a biopsy region in an object to be examined based on two radiographic images which are acquired in a stereographic image capturing process, an irradiated field calculator calculates a new irradiated field covering the biopsy region based on the calculated three-dimensional position of the biopsy region and two angles at which a radiation source is disposed in the stereographic image capturing process, and a collimator controller controls a collimator to change the irradiated field of the radiation to the new irradiated field in a next stereographic image capturing process.

8 Claims, 10 Drawing Sheets

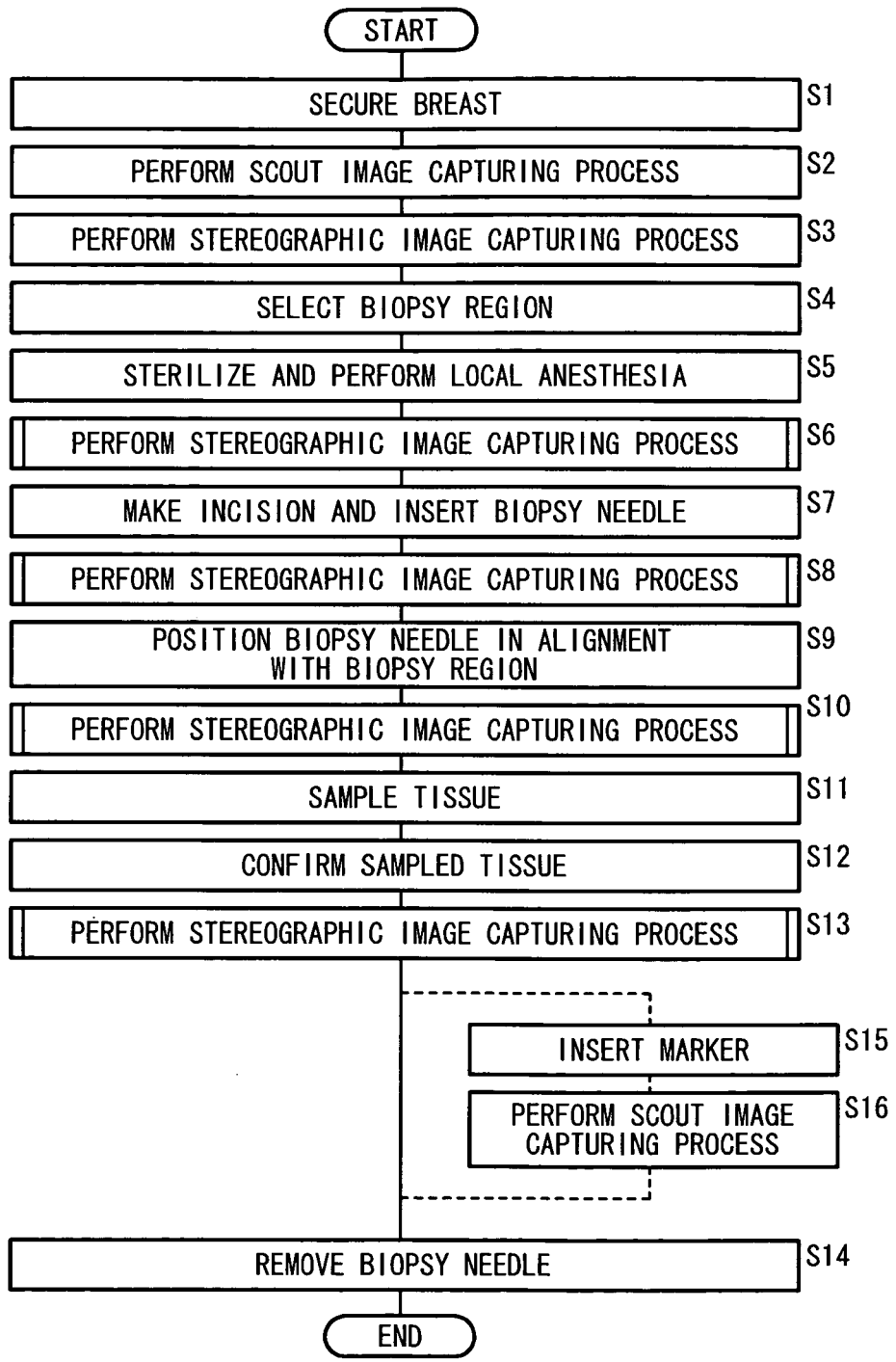

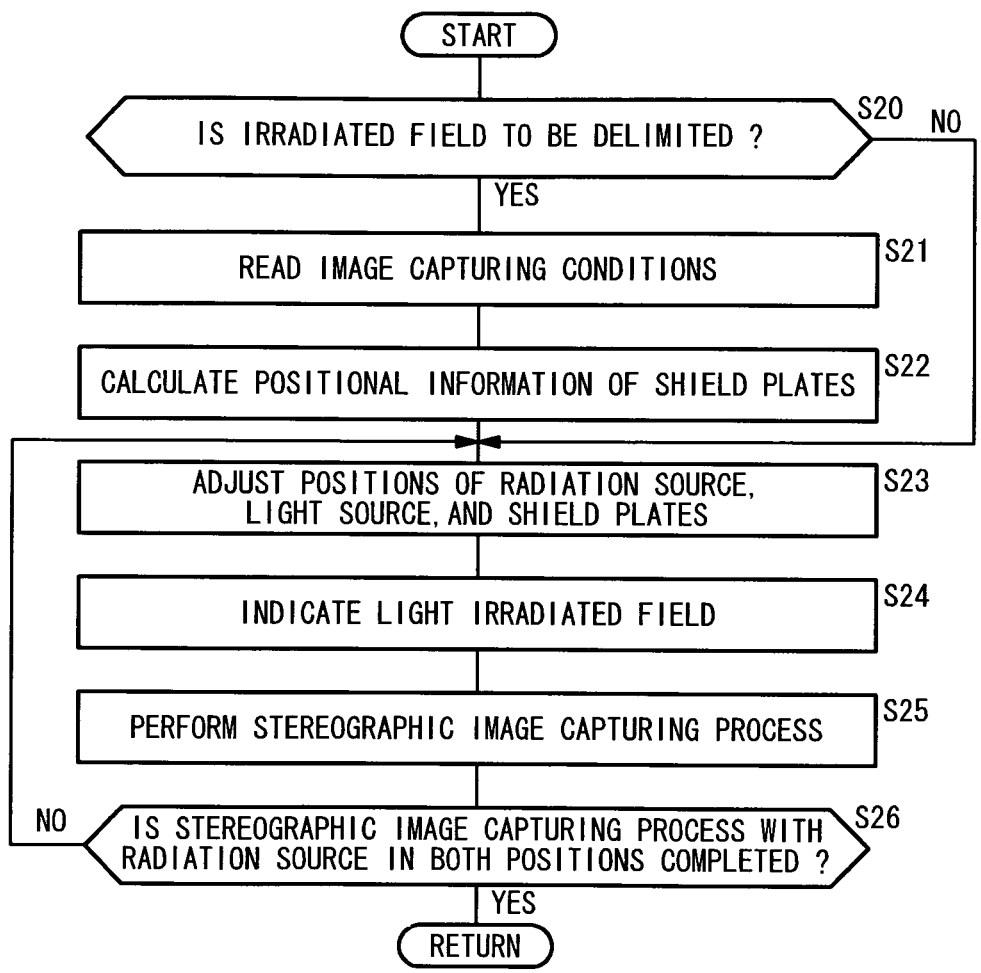

RADIOGRAPHIC IMAGE CAPTURING APPARATUS AND RADIOGRAPHIC IMAGE CAPTURING METHOD

CROSS-REFERENCE TO RELATED APPLICATION

This application is based upon and claims the benefit of priority from Japanese Patent Application No. 2009-224505 filed on Sep. 29, 2009, of which the contents are incorporated herein by reference.

BACKGROUND OF THE INVENTION

1. Field of the Invention

The present invention relates to a radiographic image capturing apparatus and a radiographic image capturing method for irradiating an object to be examined of a subject with radiation emitted from a radiation source while an irradiated field of the radiation on a radiation detector is being delimited by a collimator, and converting the radiation that has passed through the object to be examined into a radiographic image with the radiation detector.

2. Description of the Related Art

There have heretofore been developed biopsy apparatus for sampling a tissue of a biopsy region (e.g., a lesion region in a subject's breast) in an object to be examined of a subject and thoroughly examining the sampled tissue for a disease diagnosis. In order to sample the tissue reliably, the biopsy region needs to have its three-dimensional position specified in advance.

It has been customary to carry out a stereographic image capturing process on a radiographic image capturing apparatus by irradiating the object to be examined with radiation from a radiation source disposed at two different angular positions and detecting the radiation that has passed through the object to be examined with a radiation detector to acquire two radiographic images of the object to be examined, and calculate a three-dimensional position of the biopsy region based on the acquired two radiographic images.

The irradiated field of the radiation on the radiation detector is delimited in advance by a collimator which is disposed between the radiation source and the radiation detector, or more specifically the object to be examined that is positioned on the side of the radiation detector which faces the radiation source (see Japanese Utility Model Publication No. 54-032458 and Japanese Laid-Open Patent Publication No. 08-107891).

As described above, the three-dimensional position of the biopsy region needs to be specified in advance in order to sample the tissue of the biopsy region reliably. Therefore, if the radiation is applied to at least the biopsy region in the stereographic image capturing process, then it is possible to calculate the three-dimensional position of the biopsy region based on the two radiographic images which include the biopsy region.

However, the radiographic image capturing apparatus according to the related art has the irradiated field of the radiation fixed in all stereographic image capturing processes. In other words, the collimator does not adjust the irradiated field before and after each of the stereographic image capturing processes. During the stereographic image capturing processes, therefore, the radiation is also applied to body regions of the subject which have nothing to do with the calculation of the three-dimensional position of the biopsy region, and hence the subject is unduly exposed to the radiation.

In the stereographic image capturing process, the biopsy region may not be included in the two radiographic images or either one of the two radiographic images due to a movement or positional or angular change of the object to be examined between stereographic image capturing processes or due to angular errors of the radiation source at the two angular positions. If the biopsy region is included in only one or neither of the two radiographic images, then the three-dimensional position of the biopsy region cannot be calculated accurately. As a result, the tissue of the biopsy region cannot properly be sampled by the biopsy apparatus.

SUMMARY OF THE INVENTION

It is an object of the present invention to provide a radiographic image capturing apparatus and a radiographic image capturing method which prevent a subject from being unduly exposed to radiation and accurately calculate the three-dimensional position of a biopsy region in an object to be examined by reliably performing a stereographic image capturing process on the biopsy region.

To achieve the above object, there is provided in accordance with the present invention a radiographic image capturing apparatus comprising a radiation source for applying radiation to an object to be examined of a subject, a radiation detector for detecting the radiation that has passed through the object and converting the detected radiation into a radiographic image, a collimator for delimiting an irradiated field of the radiation with respect to the radiation detector, the collimator being disposed between the radiation source and the object, a biopsy region positional information calculating unit for calculating a three-dimensional position of a biopsy region in the object based on two radiographic images which are acquired by the radiation detector in a stereographic image capturing process in which the radiation source disposed at least at two angles applies the radiation to the object, an irradiated field calculating unit for calculating a new irradiated field covering the biopsy region based on the calculated three-dimensional position of the biopsy region and the two angles, and a collimator control unit for controlling the collimator to change the irradiated field of the radiation in a next stereographic image capturing process to the new irradiated field.

According to the present invention, there is also provided a radiographic image capturing method comprising the steps of performing a stereographic image capturing process by applying radiation from a radiation source disposed at least at two angles to an object to be examined of a subject while an irradiated field of the radiation with respect to the radiation detector is being delimited by a collimator, detecting, with the radiation detector, the radiation applied from the radiation source disposed at the two angles to acquire two radiographic images, calculating, with a biopsy region positional information calculating unit, a three-dimensional position of a biopsy region in the object based on the two radiographic images, calculating, with an irradiated field calculating unit, a new irradiated field covering the biopsy region based on the calculated three-dimensional position of the biopsy region and the two angles, and controlling the collimator with a collimator control unit to change the irradiated field of the radiation in a next stereographic image capturing process to the new irradiated field.

With the radiographic image capturing apparatus and the radiographic image capturing method described above, based on the three-dimensional position of the biopsy region which is obtained in a present stereographic image capturing process, an irradiated field (new irradiated field) of the radiation in a next stereographic image capturing process is calculated, and the next stereographic image capturing process is performed with the calculated new irradiated field. Since the radiation is applied in the new irradiated field around the biopsy region in the next stereographic image capturing process, the radiation is prevented from being applied to body regions of the subject which have nothing to do with the calculation of the three-dimensional position of the biopsy region, and hence the subject is prevented from being unduly exposed to the radiation.

Even if the object is moved or positionally or angularly changed between stereographic image capturing processes or the radiation source disposed at the two angles suffers angular errors, since the new irradiated field around the biopsy region is irradiated with the radiation in the next stereographic image capturing process, two radiographic images acquired in the next stereographic image capturing process reliably cover the biopsy region. Consequently, it is possible to perform a stereographic image capturing process on the biopsy region and to accurately calculate the three-dimensional position of the biopsy region regardless of a movement or positional or angular change of the object or angular errors of the radiation source.

According to the present invention, therefore, the subject is prevented from being unduly exposed to the radiation, and a stereographic image capturing process is reliably performed on the biopsy region in the object to be examined to accurately calculate the three-dimensional position of the biopsy region.

The application of the radiation to the object from the radiation source at the two angles, the calculation of the three-dimensional position of the biopsy region by the biopsy region positional information calculating unit, the calculation of the new irradiated field by the irradiated field calculating unit, and the changing of the irradiated field of the radiation to the new irradiated field by the collimator control unit may successively be carried out repeatedly.

Accordingly, the present stereographic image capturing process can be performed while reflecting the result (the three-dimensional position of the biopsy region) of the previous stereographic image capturing process, and the next stereographic image capturing process is performed while reflecting the result of the present stereographic image capturing process. As a result, even if the object is moved or positionally or angularly changed between stereographic image capturing processes or the radiation source disposed at the two angles suffers angular errors, the radiation source can apply the radiation to the object to be examined within a new irradiated field around the biopsy region. In other words, the radiation source applies the radiation to the object while at the same time tracking the biopsy region.

The radiographic image capturing apparatus may further comprise irradiated field calculation control unit for selectively enabling the irradiated field calculating unit to calculate the new irradiate field or disabling the irradiated field calculating unit from calculating the new irradiate field.

If any movement or positional or angular change of the object between stereographic image capturing processes is small, then the irradiated field calculation control unit enables the irradiated field calculating unit to calculate the new irradiated field for thereby preventing the subject from being unduly exposed to the radiation. On the other hand, if the object is greatly moved or positionally or angularly changed between stereographic image capturing processes, then the irradiated field calculation control unit disables the irradiated field calculating unit from calculating the new irradiated field, and the radiation is applied to the object to be examined in a wider irradiated field, for thereby allowing the biopsy region to be reliably covered by a radiographic image.

The radiographic image capturing apparatus may further comprise a light source for spotlighting the radiation detector to indicate the irradiated field thereon, before the radiation source applies the radiation to the object.

It is thus easy to confirm whether there exists any obstacle to a stereographic image capturing process between the radiation source and the object to be examined, before the stereographic image capturing process is carried out.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 9 is a flowchart of an operation sequence of the mammographic apparatus; and FIG. 10 is a flowchart of an operation sequence of second and subsequent stereographic image capturing processes.

DESCRIPTION OF THE PREFERRED EMBODIMENTS

Figure 1:
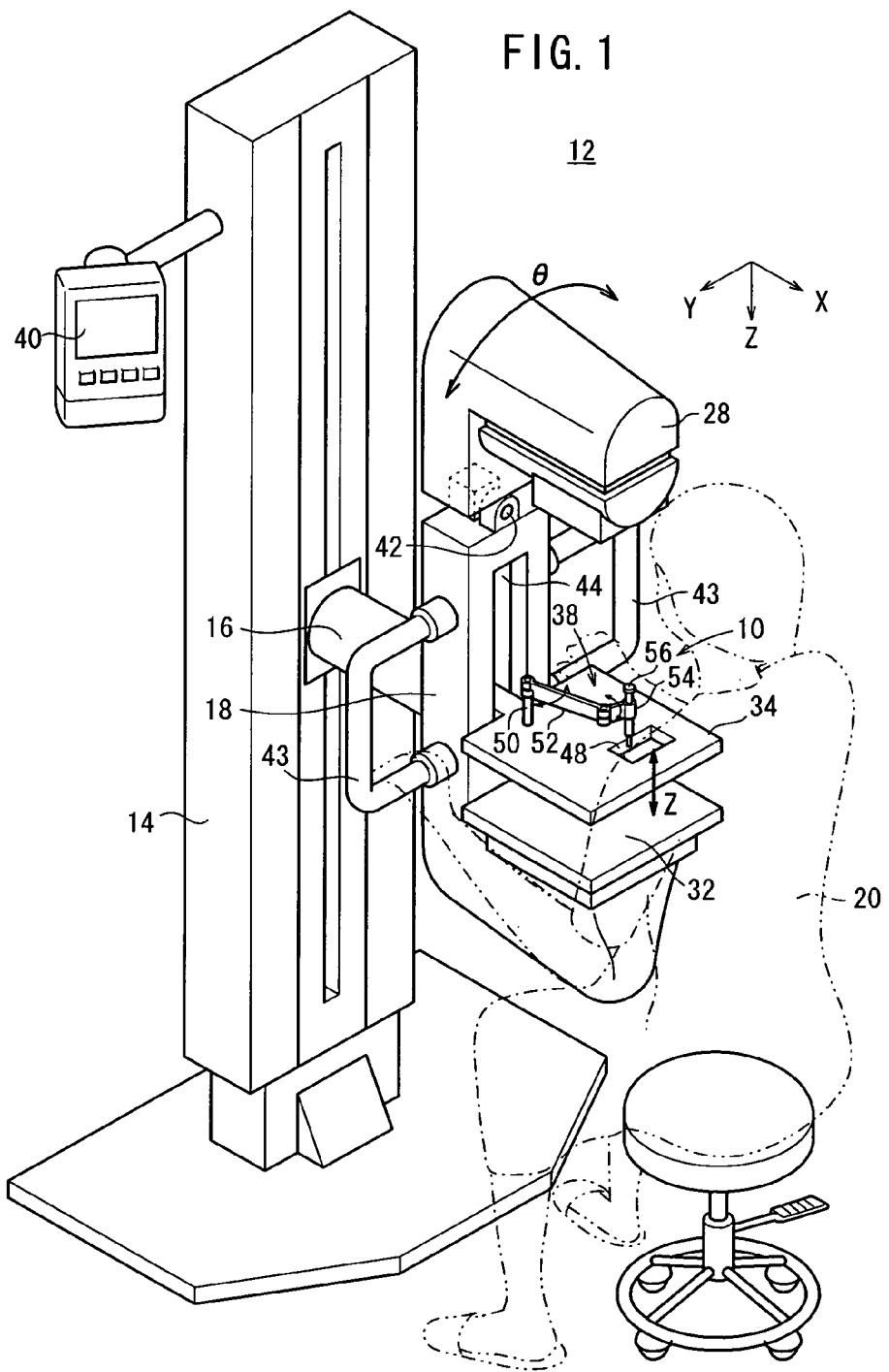
FIG. 1 is a perspective view of a mammographic apparatus as a radiographic image capturing apparatus according to an embodiment of the present invention.

A radiographic image capturing apparatus and a radiographic image capturing method according to a preferred embodiment of the present invention will be described below with reference to FIGS. 1 through 10 of the accompanying drawings.

The basic structure of a mammographic apparatus 12 serving as the radiographic image capturing apparatus according to an embodiment of the present invention which incorporates a biopsy apparatus 10 will be described below with reference to FIGS. 1 and 2.

The mammographic apparatus 12 basically includes an upstanding base 14, a vertical arm 18 fixed to the distal end of a swing shaft 16 disposed substantially centrally on the base 14, a radiation source housing unit 28 fixed to an upper end of the arm 18 and housing therein a radiation source 26 for applying radiation 24 to a breast 22 as an object to be examined of an examinee (subject) 20, an image capturing base 32 mounted on a lower end of the arm 18 and housing therein a solid-state detector (radiation detector) 30 for detecting the radiation 24 which has passed through the breast 22, a compression plate 34 for compressing and holding the breast 22 against the image capturing base 32, and a biopsy hand assembly 38 for removing a tissue sample from a biopsy region 36 of the breast 22, the biopsy hand assembly 38 being mounted on the compression plate 34.

Figure 2:
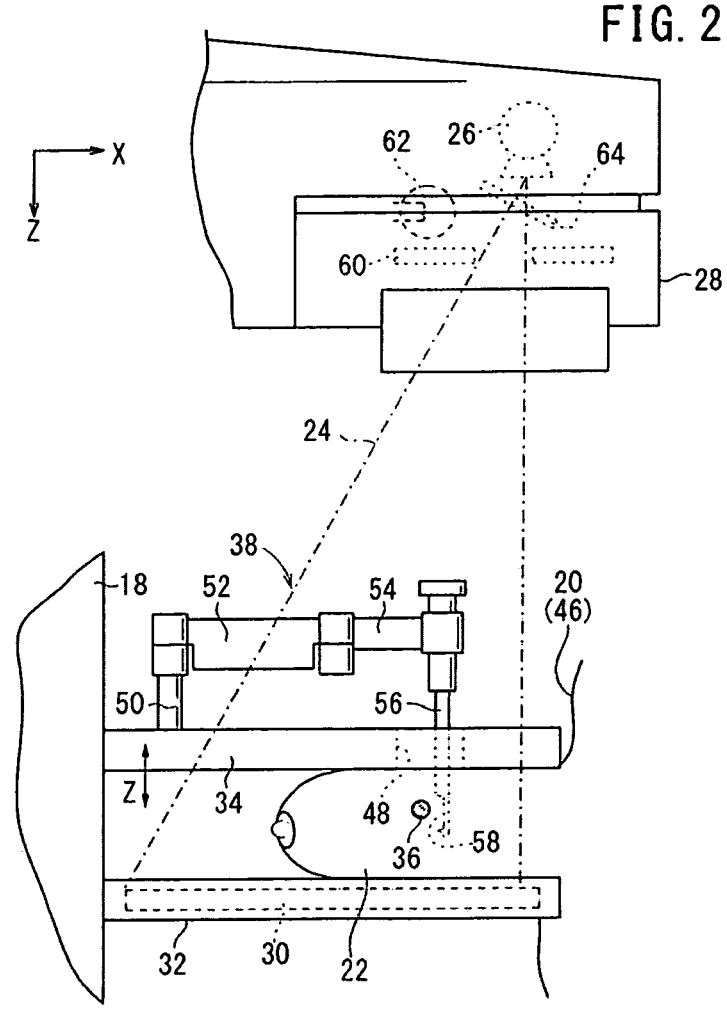
FIG. 2 is an enlarged fragmentary side elevational view of the mammographic apparatus shown in FIG. 1.

In FIGS. 1 and 2, the mammographic apparatus 12 applies the radiation 24 to the breast 22 of the examinee 20 and a sample tissue is removed from the biopsy region 36, while the breast 22 of the examinee 20 who is in a sitting position is being compressed and secured by the compression plate 34 and the image capturing base 32. To the base 14, there is connected a display control panel 40 for displaying image capturing conditions representing an image capturing region, etc. of the examinee 20, the ID information of the examinee 20, etc., and setting these items of information, if necessary.

As shown in FIG. 1, when the arm 18, to which the radiation source housing unit 28 and the image capturing base 32 are secured, is angularly moved about the swing shaft 16, the direction of the radiation source housing unit 28 and the image capturing base 32 with respect to the breast 22 of the examinee 20 is adjusted. The radiation source housing unit 28 is operatively coupled to the arm 18 by a hinge 42 and can be turned about the hinge 42 in the directions indicated by the arrow θ independently of the image capturing base 32.

The arm 18 has a groove 44 defined vertically in a side (front side) thereof which faces the examinee 20 in the direction indicated by the arrow X. The groove 44 extends along the direction indicated by the arrow Z. Handles 43 are mounted on the respective sides of the arm 18 which face away from each other along the direction indicated by the arrow Y. The handles 43 are gripped by the examinee 20. As shown in FIGS. 1 and 2, the compression plate 34 has a proximal end inserted in the groove 44 and held in interfitting engagement with a mount, not shown, disposed in the arm 18. The compression plate 34 that is thus coupled to the arm 18 is disposed between the radiation source housing unit 28 and the image capturing base 32. The compression plate 34 is displaceable in unison with the mount along the arm 18 in the directions indicated by the arrow Z when the mount is displaced along the groove 44 in the directions indicated by the arrow Z.

The compression plate 34 has an opening 48 defined therein near a chest wall 46 (see FIG. 2) of the examinee 20, for allowing the biopsy hand assembly 38 to remove a tissue sample from the biopsy region 36 of the breast 22. The biopsy hand assembly 38 serves as part of the biopsy apparatus 10 which is incorporated in the mammographic apparatus 12. The biopsy hand assembly 38 comprises a post 50 fixedly mounted on the compression plate 34, a first arm 52 having an end pivotally supported on the post 50 and angularly movable about the post 50 along the surface of the compression plate 34, and a second arm 54 having an end pivotally supported on the other end of the first arm 52 and angularly movable about the other end of the first arm 52 along the surface of the compression plate 34. A biopsy needle 56 is mounted on the other end of the second arm 54 for movement in the directions indicated by the arrow Z.

As shown in FIG. 2, the biopsy needle 56 has a sampler 58 for sampling under suction a tissue (e.g., a calcified tissue) from the biopsy region 36, which is a lesion area (e.g., a calcified area) of the breast 22. The sampler 58 of the biopsy needle 56 can be moved to a position in the vicinity of the biopsy region 36 when the first arm 52 and the second arm 54 of the biopsy hand assembly 38 are moved in an X-Y plane parallel to the surface of the compression plate 34 and the biopsy needle 56 is moved in the directions indicated by the arrow Z.

The radiation source housing unit 28 also houses therein, in addition to the radiation source 26, a collimator 60 for delimiting an irradiated field of the radiation 24 emitted from the radiation source 26, a light source 62 and a mirror 64 for spotlighting the breast 22 to indicate the irradiated field of the radiation 24 thereon before the radiation 24 is actually emitted from the radiation source 26. The mirror 64 is disposed between the radiation source 26 and the collimator 60 and is made of a material permeable to the radiation 24.

Figure 3:
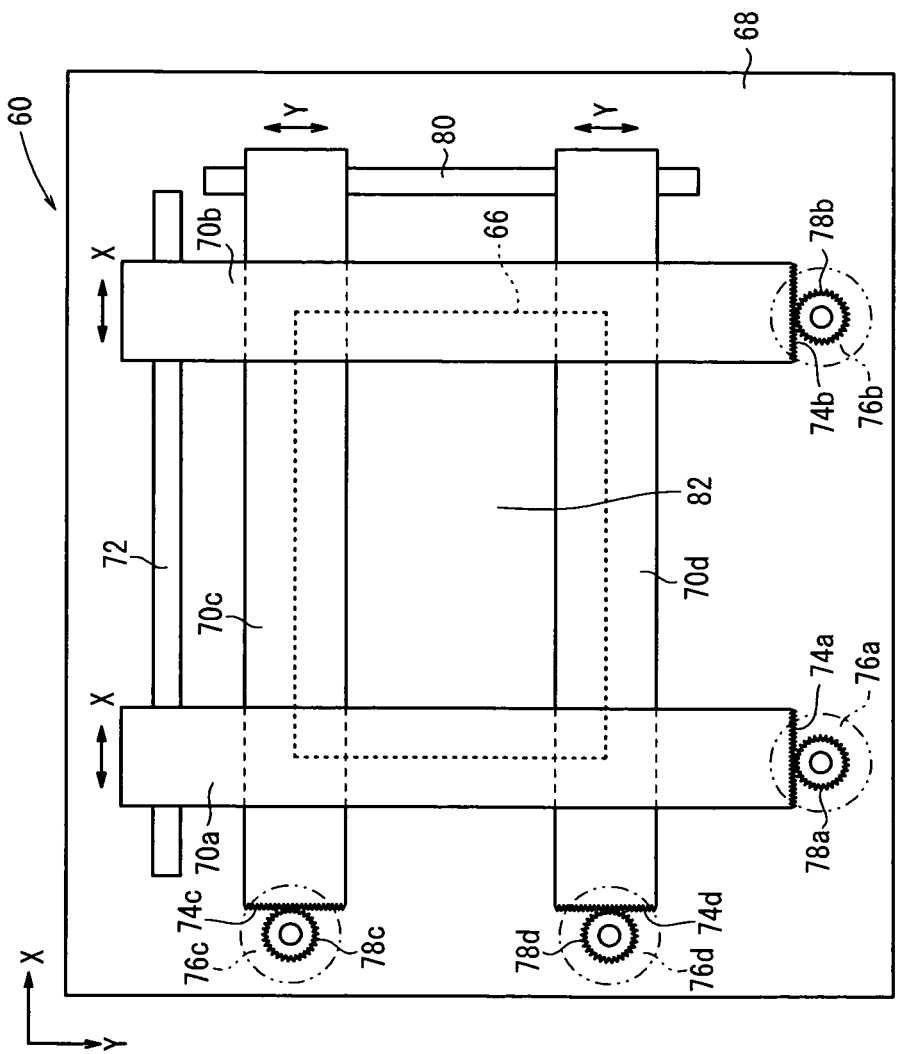
FIG. 3 is a plan view of a collimator shown in FIG. 2.

As shown in FIG. 3, the collimator 60 comprises a base 68 having a rectangular opening 66 defined therein, and four elongate rectangular shield plates 70a, 70b, 70c, 70d mounted on the base 68 for independent movement in the directions indicated by the arrows X, Y. The shield plates 70a, 70b have ends movably engaging a guide rail 72 on the base 68 and opposite ends including racks 74a, 74b which are held in mesh with respective pinions 78a, 78b rotatable by respective motors 76a, 76b mounted on the base 68. Similarly, the shield plates 70c, 70d have ends movably engaging a guide rail 80 on the base 68 and opposite ends including racks 74c, 74d which are held in mesh with respective pinions 78c, 78d rotatable by respective motors 76c, 76d mounted on the base 68. The shield plates 70a, 70b, 70c, 70d delimit the position and area of an opening 82 for the radiation 24 to pass therethrough.

Before the radiation 24 is actually emitted from the radiation source 26, the light source 62 emits illuminating light, not shown. The illuminating light emitted from the light source 62 is reflected by the mirror 64 toward the collimator 60 through the opening 82 of the collimator 60 to the outside (near the breast 22).

Figure 4:
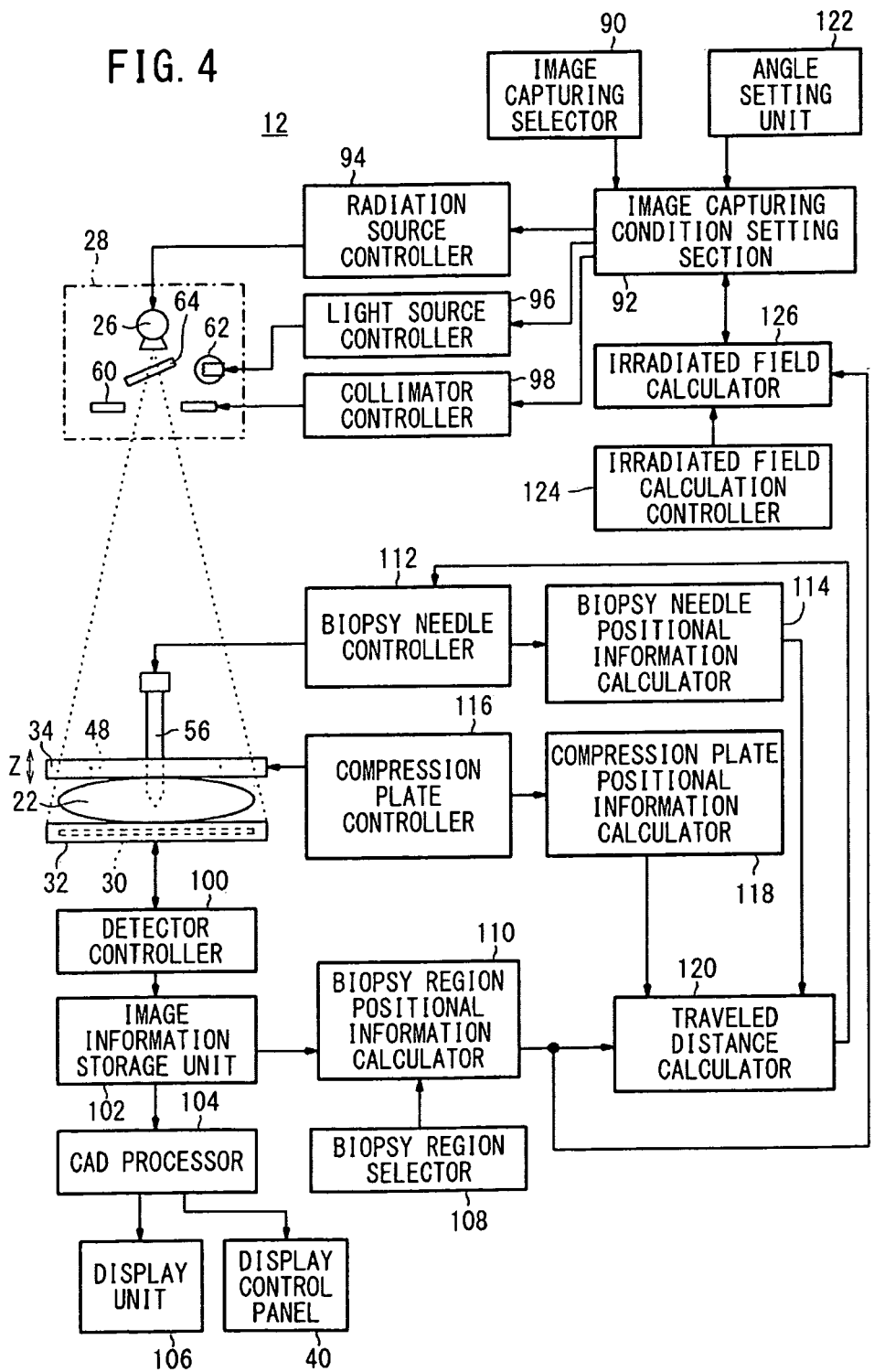
FIG. 4 is a block diagram of the mammographic apparatus shown in FIG. 1.

FIG. 4 shows in block diagram the mammographic apparatus 12 including the biopsy apparatus 10.

As shown in FIG. 4, the mammographic apparatus 12 includes an image capturing selector 90, an image capturing condition setting section 92, a radiation source controller 94, a light source controller 96, a collimator controller (collimator control unit) 98, a detector controller 100, an image information storage unit 102, a CAD (Computer Aided Diagnosis) processor 104, a display unit 106, a biopsy region selector 108, a biopsy region positional information calculator (biopsy region positional information calculating unit) 110, a biopsy needle controller 112, a biopsy needle positional information calculator 114, a compression plate controller 116, a compression plate positional information calculator 118, a traveled distance calculator 120, an angle setting unit 122, an irradiated field calculation controller (irradiated field calculation control unit) 124, and an irradiated field calculator (irradiated field calculating unit) 126.

The biopsy hand assembly 38, the biopsy needle 56, the opening 48, the biopsy region selector 108, the biopsy needle controller 112, the biopsy needle positional information calculator 114, and the traveled distance calculator 120 jointly make up the biopsy apparatus 10. The biopsy apparatus 10 which is incorporated in the mammographic apparatus 12 is capable of sampling part of a tissue of the biopsy region 36.

The image capturing condition setting section 92 sets image capturing conditions including a tube current and a tube voltage of the radiation source 26, an irradiation dose and an irradiation time of the radiation 24, an image capturing method such as a scout image capturing process or a stereographic image capturing process (see FIGS. 5 through 7), and an imaging sequence. The stereographic image capturing process includes details about stereographic image capturing angles (two of 0°, +θ1, and −θ1 in FIGS. 5 through 7), three-dimensional positions of the radiation source 26 at the imaging capturing angles, radiation angles (θB1, θB2, θC1, θC2) which delimit an irradiated field of the radiation 24 when the radiation 24 is applied at the image capturing angles, and positional information of the shield plates 70a through 70d in a stereographic image capturing process.

The three-dimensional position of the radiation source 26 specifies an image capturing angle, and the positional information of the shield plates 70a through 70d specifies a radiating angle. Therefore, the three-dimensional position of the radiation source 26 or the image capturing angle, and the positional information of the shield plates 70a through 70d or the radiating angle may be set at least in the image capturing condition setting section 92 as image capturing conditions for the image capturing method representative of the stereographic image capturing process.

The radiation source controller 94 energizes the radiation source 26 according to the image capturing conditions. The light source controller 96 energizes the light source 62 according to the image capturing conditions before the radiation source 26 is energized. The collimator controller 98 energizes the motors 76a through 76d (see FIG. 3) of the collimator 60 according to the image capturing conditions to displace the shield plates 70a through 70d for thereby delimiting the position and area of the opening 82 for the radiation 24 to pass therethrough.

The biopsy needle controller 112 controls the biopsy hand assembly 38 (see FIGS. 1 and 2) to move the biopsy needle 56 to a desired position. The compression plate controller 116 moves the compression plate 34 in the directions indicated by the arrow Z. The detector controller 100 controls the solid-state detector 30 to store a radiographic image converted thereby from the radiation 24 into the image information storage unit 102.

Basic image capturing methods (a scout image capturing process and a stereographic image capturing process) for capturing a radiographic image to be stored in the image information storage unit 102 will be described below with reference to FIGS. 5 and 6.

The mammographic apparatus 12 performs a scout image capturing process (see FIG. 5) in which the radiation source 26 disposed on the vertical axis (central axis 130a of the radiation source 26) of the solid-state detector 30 applies radiation 24a to the breast 22 or a stereographic image capturing process (see FIG. 6) in which the radiation source 26 disposed obliquely to the central axis 130a applies radiation 24b, 24c to the breast 22 along respective central axes 130b, 130c of the obliquely disposed radiation source 26. The solid-state detector 30 detects the radiation 24a, 24b, 24c that has passed through the breast 22 in the scout image capturing process or the stereographic image capturing process and converts the detected radiation 24a, 24b, 24c into respective radiographic images.

In the mammographic apparatus 12, the radiation source 26 applies the radiation 24a, 24b, 24c to the breast 22 when the biopsy region 36 is located on the respective central axes 130a, 130b, 130c.

Figure 5:
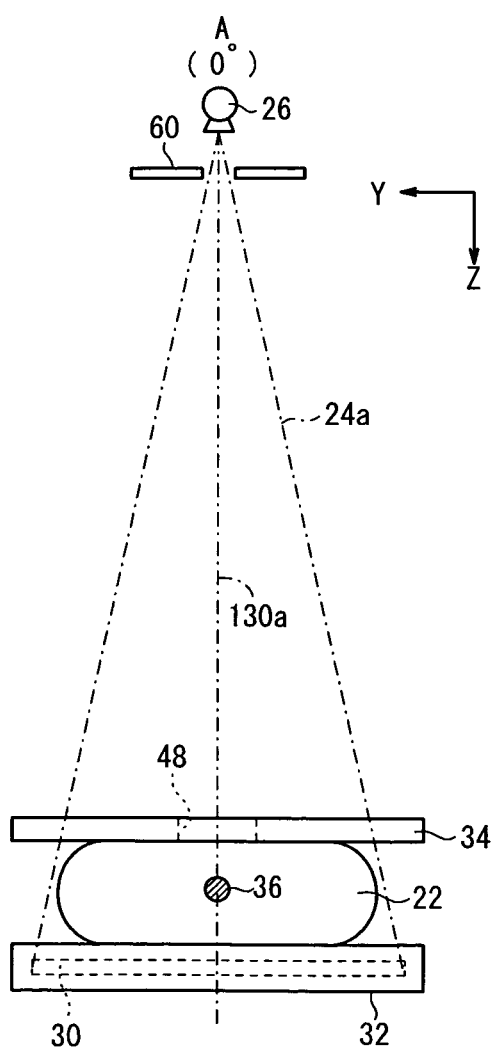
FIG. 5 is a schematic front elevational view illustrative of a scout image capturing process.

FIG. 5 illustrates the scout image capturing process which captures a single radiographic image. In the scout image capturing process, the radiation source 26 is located at an image capturing angle of $\theta=0°$ with respect to the solid-state detector 30. The position of the radiation source 26 at the image capturing angle of $\theta=0°$ in the scout image capturing process is referred to as "position A".

Figure 6:
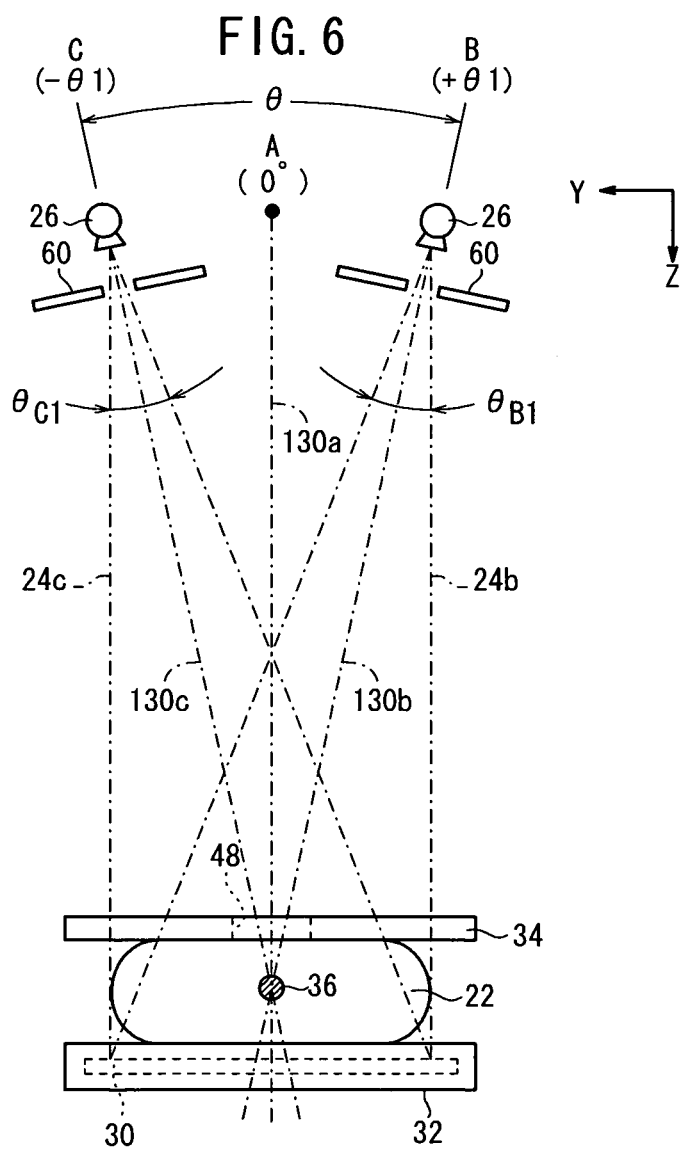
FIG. 6 is a schematic front elevational view illustrative of a stereographic image capturing process with an unrestricted irradiated field of radiation.

FIG. 6 illustrates the stereographic image capturing process which captures two radiographic images. In the stereographic image capturing process, the radiation source 26 is located at two image capturing angles of $+\theta1, -\theta1$ with respect to the solid-state detector 30. The positions of the radiation source 26 at the image capturing angles of $+\theta1, -\theta1$ in the stereographic image capturing process are referred to as "position B" and "position C", respectively. In FIG. 6, the irradiated range and irradiated field of the radiation 24b which is emitted from the radiation source 26 that is located in the position B at the image capturing angle of $+\theta1$ are defined by an angle (radiating angle) $\theta B1$, and the irradiated range and irradiated field of the radiation 24c which is emitted from the radiation source 26 that is located in the position C at the image capturing angle of $-\theta1$ are defined by an angle (radiating angle) $\theta C1$.

The mammographic apparatus 12 may perform scout image capturing processes and stereographic image capturing processes according to any desired imaging sequence. The radiation source 26 is moved between the position A, the position B, the position C when the radiation source housing unit 28 is turned about the hinge 42.

In the above stereographic image capturing process, the radiation source 26 applies the radiation 24b, 24c when it is located in the respective positions B, C. However, the mammographic apparatus 12 may perform a stereographic image capturing process in which the radiation source 26 applies the radiation 24a, 24b when it is located in the respective positions A, B, and/or a stereographic image capturing process in which the radiation source 26 applies the radiation 24a, 24c when it is located in the respective positions A, C.

When the mammographic apparatus 12 performs a scout image capturing process, the image information storage unit 102 stores a single radiographic image captured at a single image capturing angle. When the mammographic apparatus 12 performs a stereographic image capturing process, the image information storage unit 102 stores two radiographic images captured at two respective image capturing angles (stereographic angles).

In FIG. 4, the CAD processor 104 processes a radiographic image stored in the image information storage unit 102 and displays the processed radiographic image on the display unit 106 and the display control panel 40.

The biopsy region selector 108 comprises a pointing device such as a mouse or the like. The doctor or radiological technician in charge who has seen the displayed contents, e.g., two radiographic images produced by a stereographic image capturing process, on the display unit 106 and/or the display control panel 40 can select one, from which a tissue is to be removed, of a plurality of biopsy regions 36 in the displayed two radiographic images, using the pointing device as the biopsy region selector 108. Specifically, the doctor or radiological technician selects a biopsy region 36 in one of the two radiographic images and also selects a corresponding biopsy region 36 in the other of the two radiographic images.

The biopsy region positional information calculator 110 calculates the three-dimensional position of the selected biopsy region 36 based on the positions of the selected biopsy region 36 in the two radiographic images that are selected by the biopsy region selector 108. The three-dimensional position of the selected biopsy region 36 can be calculated according to a known three-dimensional position calculating scheme for the stereographic image capturing process.

The biopsy needle positional information calculator 114 calculates the positional information of the tip end of the biopsy needle 56 which has been moved by the biopsy needle controller 112. When a tissue is to be sampled from the biopsy region 36, the biopsy needle positional information calculator 114 calculates the position of the tip end of the biopsy needle 56 before it samples the tissue from the biopsy region 36, i.e., the position of the tip end of the biopsy needle 56 before it pierces the breast 22.

The compression plate positional information calculator 118 calculates the positional information of the compression plate 34 which has been moved with respect to the image capturing base 32 by the compression plate controller 116.

Since the compression plate 34 presses the breast 22 with respect to the image capturing base 32 and holds the breast 22 in the pressed state, the positional information of the compression plate 34 represents the thickness information of the breast 22 as it is pressed.

The traveled distance calculator 120 calculates the distance by which the biopsy needle 56 is to move with respect to the biopsy region 36, based on the three-dimensional position of the biopsy region 36 which has been calculated by the biopsy region positional information calculator 110, the position of the tip end of the biopsy needle 56 which has been calculated by the biopsy needle positional information calculator 114, and the position of the compression plate 34 which has been calculated by the compression plate positional information calculator 118 (the thickness of the breast 22). Based on the calculated distance by which the biopsy needle 56 is to move with respect to the biopsy region 36, the biopsy needle controller 112 moves the biopsy needle 56 for removing a tissue sample from the selected biopsy region 36.

The image capturing selector 90 comprises a pointing device such as a mouse or the like or a keyboard. The doctor or radiological technician changes an image capturing method preset in the image capturing condition setting section 92 to another image capturing method, using the pointing device or the keyboard. Even after radiographic images have been captured, the doctor or radiological technician can select a radiographic image to be used by the biopsy region positional information calculator 110 to calculate the three-dimensional position, using the pointing device or the keyboard.

The angle setting unit 122 comprises a pointing device such as a mouse or the like or a keyboard. The doctor or radiological technician sets image capturing angles and/or radiating angles for a stereographic image capturing process in the image capturing condition setting section 92, or changes the image capturing angles and/or radiating angles already set in the image capturing condition setting section 92, using the pointing device or the keyboard.

The irradiated field calculator 126 reads the image capturing conditions for a stereographic image capturing process that have been set in the image capturing condition setting section 92, and calculates an irradiated field of the radiation 24 for a next stereographic image capturing process based on the read image capturing conditions and the three-dimensional position of the biopsy region 36 calculated by the biopsy region positional information calculator 110.

In this case, the biopsy region positional information calculator 110 calculates the three-dimensional position of the biopsy region 36 in the previous stereographic image capturing process based on the two radiographic images captured in the previous stereographic image capturing process and stored in the image information storage unit 102, and outputs the calculated three-dimensional position to the irradiated field calculator 126. Therefore, the irradiated field calculator 126 reads the image capturing conditions for the previous stereographic image capturing process that have been set in the image capturing condition setting section 92.

Specifically, the irradiated field calculator 126 calculates the irradiated range and irradiated field of the radiation 24 in a next stereographic image capturing process, i.e., the positions of the shield plates 70a through 70d (the position and area of the opening 82 through which the radiation 24 passes), such that the biopsy region 36 will be located on the central axes 130b, 130c and be included in the irradiated range of the radiation 24, using the three-dimensional positions of the radiation source 26 at the two image capturing angles, the positional information of the shield plates 70a through 70d in the previous stereographic image capturing process, and the three-dimensional position of the biopsy region 36 in the previous stereographic image capturing process, among the image capturing conditions of the previous stereographic image capturing process.

Since the positional information of the shield plates 70a through 70d corresponds to the radiating angle, the irradiated field calculator 126 indirectly calculates the radiating angle which defines the irradiated field of the radiation 24 by calculating the positions of the shield plates 70a through 70d.

The irradiated field calculator 126 sets the calculated positional information of the shield plates 70a through 70d as new image capturing conditions for a next stereographic image capturing process in the image capturing condition setting section 92, thus updating the setting contents of image capturing condition setting section 92.

Figure 7:
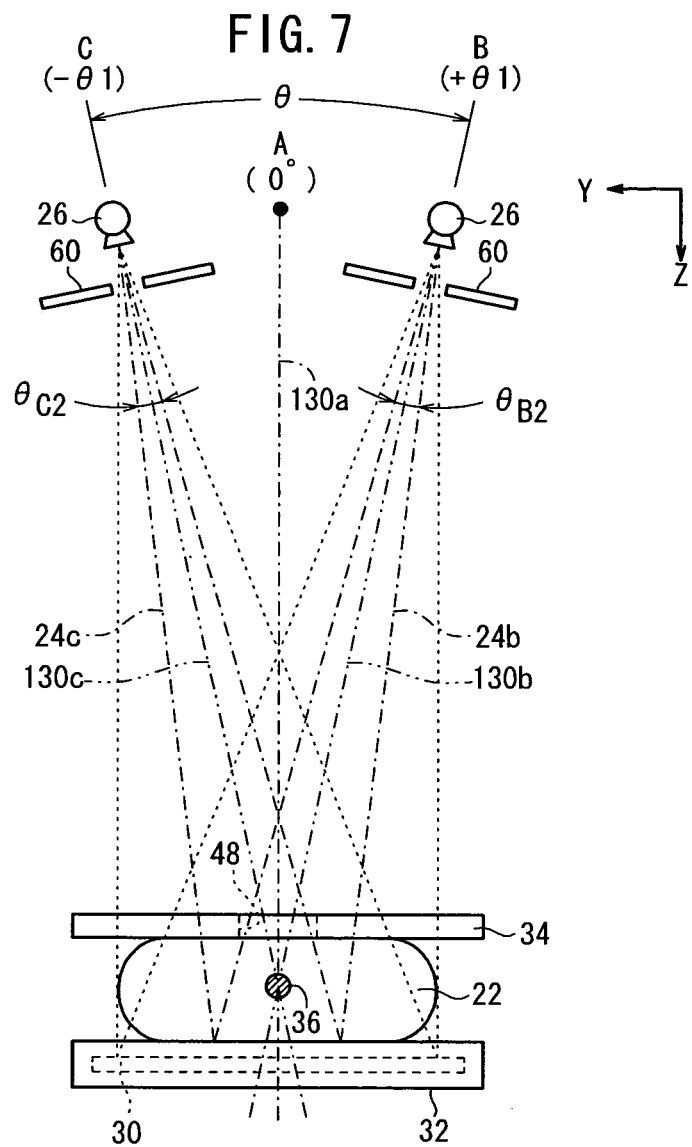
FIG. 7 is a schematic front elevational view illustrative of a stereographic image capturing process with a restricted irradiated field of radiation.
Figure 8:
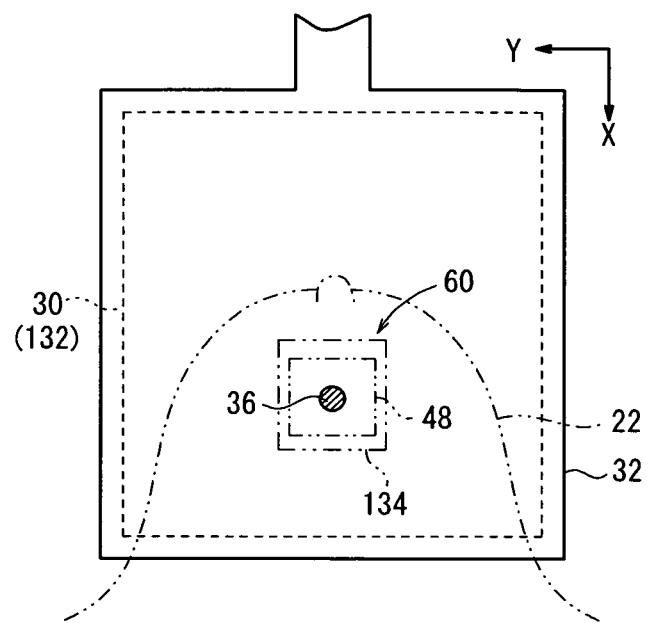
FIG. 8 is a plan view showing an irradiated field of radiation.

FIG. 7 shows, by way of example, irradiated ranges (broken lines) of the radiation 24b, 24c in a previous stereographic image capturing process and irradiated ranges (one-dot-and-dash lines) of the radiation 24b, 24c in a next stereographic image capturing process.

In a stereographic image capturing process carried out by the mammographic apparatus 12, insofar as the biopsy region 36 is positioned within the irradiated ranges of the radiation 24b, 24c, the three-dimensional position of the biopsy region 36 can reliably be calculated based on the two radiographic images.

According to the present embodiment, in order to avoid undue exposure of the examinee 20, i.e., the breast 22, to the radiation, the irradiated ranges of the radiation 24b, 24c for the next stereographic image capturing process (see FIG. 7) are made smaller than the irradiated ranges of the radiation 24b, 24c for the previous stereographic image capturing process, based on the results of the previous stereographic image capturing process (see FIG. 6), and then the next stereographic image capturing process is carried out. In other words, the radiating angles which define the irradiated ranges of the radiation 24b, 24c are changed from θB1, θC1 (the previous stereographic image capturing process) to θB2, θC2 (the next stereographic image capturing process) (θB1>θ2, θC1>θC2). As a result, the irradiated ranges of the radiation 24b, 24c are restricted from a range 132 (the previous stereographic image capturing process) to a range 134 (the next stereographic image capturing process) (see FIG. 8).

In FIG. 4, the irradiated field calculation controller 124 comprises a pointing device such as a mouse or the like or a keyboard. The doctor or radiological technician can enable the irradiated field calculator 126 to carry out a calculating process for calculating an irradiated field of the radiation 24, i.e., can perform the calculating process, or can disable the irradiated field calculator 126, i.e., can stop the calculating process, using the pointing device of the keyboard.

The mammographic apparatus 12 according to the present embodiment is basically constructed as described above. Operation of the mammographic apparatus 12 to perform a radiographic image capturing method according to the embodiment will be described below with reference to flowcharts shown in FIGS. 9 and 10.

Before radiographic images are captured, image capturing conditions including a tube current and a tube voltage depending on the breast 22, an irradiation dose and an irradiation time of the radiation 24, an image capturing method, and an imaging sequence are set in the image capturing condition setting section 92. Image capturing angles and radiating angles are set by the angle setting unit 122, and the image capturing method is set by the image capturing selector 90. The doctor or radiological technician operates the irradiated field calculation controller 124 to disable the irradiated field calculator 126 to stop its processing function.

In step S1, the doctor or radiological technician positions the breast 22 of the examinee 20. Specifically, the doctor or radiological technician places the breast 22 in a predetermined position on the image capturing base 32, i.e., a position facing the opening 48, and operates the compression plate controller 116 to move the compression plate 34 toward the image capturing base 32 in the direction indicated by the arrow Z, compressing and positioning the breast 22.

The breast 22 is now compressed and secured by the image capturing base 32 and the compression plate 34. The compression plate positional information calculator 118 calculates the positional information of the compression plate 34 with respect to the image capturing base 32, and outputs the calculated positional information to the traveled distance calculator 120.

After the above preparatory process is completed, the mammographic apparatus 12 energizes the radiation source 26 to perform a scout image capturing process on the breast 22 in step S2.

Specifically, the radiation source housing unit 28 is turned about the hinge 42 (see FIG. 1) to move the radiation source 26 to the position A (see FIG. 5). Thereafter, the collimator controller 98 energizes the motors 76a through 76d (see FIG. 3) of the collimator 60 according to the image capturing conditions of the scout image capturing process from the image capturing condition setting section 92. The shield plates 70a through 70d are displaced to set the opening 82 to the position and area according to the image capturing conditions. Then, the light source controller 96 energizes the light source 62 to emit illuminating light. The emitted illuminating light is reflected by the mirror 64 toward the collimator 60 and passes through the opening 82 toward the breast 22. As a result, the illuminating light is applied to the compression plate 34 and so on, spotlighting the compression plate 34 to indicate the irradiated field of the radiation 24 (a light irradiated field) thereon.

After having confirmed the light irradiated field, the doctor or radiological technician turns on an exposure switch, not shown. The radiation source controller 94 now energizes the radiation source 26 placed in the position A) (0°) according to the image capturing conditions from the image capturing condition getting section 92.

The radiation 24 emitted from the radiation source 26 in the position A passes through the opening 82 out of the collimator 60, and is applied to the breast 22. The radiation 24 then passes through the breast 22, and is detected by the solid-state detector 30 as radiation representing a single radiographic image of the breast 22. The detector controller 100 controls the solid-state detector 30 to acquire a single radiographic image from the detected radiation and to store the acquired radiographic image in the image information storage unit 102. The CAD processor 104 processes the radiographic image stored in the image information storage unit 102, and displays the processed radiographic image on the display unit 106 and the display control panel 40. The doctor or radiological technician can now confirm that the breast 22 including the biopsy region 36 is positioned within a radiographic image capturing range.

In step S3, the mammographic apparatus 12 energizes the radiation source 26 to perform a stereographic image capturing process on the breast 22.

The mammographic apparatus 12 turns the radiation source housing unit 28 about the hinge 42 (see FIG. 1) to place the radiation source 26 in the position B (see FIG. 6), for example. Then, the collimator controller 98 energizes the motors 76a through 76d of the collimator 60 according to the image capturing conditions of the stereographic image capturing process from the image capturing condition setting section 92. The shield plates 70a through 70d are displaced to set the opening 82 to the position and area according to the image capturing conditions. Then, the light source controller 96 energizes the light source 62 to emit illuminating light. The emitted illuminating light is reflected by the mirror 64 toward the collimator 60 and passes through the opening 82 toward the breast 22. The illuminating light is applied to the compression plate 34 and the like, indicating a light irradiated field.

After having confirmed the light irradiated field, the doctor or radiological technician turns on the exposure switch. The radiation source controller 94 now energizes the radiation source 26 placed in the position B (+θ1) according to the stereographic image capturing conditions from the image capturing condition setting section 92.

The radiation 24b emitted from the radiation source 26 in the position B passes through the opening 82 out of the collimator 60, and is applied to the breast 22. The radiation 24b then passes through the breast 22, and is detected by the solid-state detector 30 as radiation representing a first radiographic image of the breast 22. The detector controller 100 controls the solid-state detector 30 to acquire a single radiographic image from the detected radiation and to store the acquired radiographic image as the first radiographic image in the image information storage unit 102 temporarily.

After the single radiographic image has been captured based on the radiation emitted from the radiation source 26 in the position B, the mammographic apparatus 12 moves the radiation source 26 to the position C in FIG. 6, and captures a second radiographic image of the breast 22 based on the radiation from the radiation source 26 in the position C, in a similar manner to the image capturing process in the position B described above.

The second radiographic image is acquired in the position C and stored in the image information storage unit 102. Thereafter, the CAD processor 104 processes the two radiographic images stored in the image information storage unit 102, and displays the processed radiographic images on the display unit 106 and the display control panel 40.

In step S4, the doctor or radiological technician sees the two radiographic images displayed on the display unit 106 and/or the display control panel 40, and selects a biopsy region 36 from which a tissue is to be sampled, from the biopsy regions 36 in the displayed two radiographic images by using the biopsy region selector 108 which is a pointing device such as a mouse. Then, the biopsy region positional information calculator 110 calculates the three-dimensional position of the selected biopsy region 36, and displays the calculated three-dimensional position on the display unit 106 and the display control panel 40.

In step S5, the doctor or radiological technician sterilizes and gives a local anesthesia to the breast 22 before the biopsy needle 56 pierces the breast 22.

In step S6, the mammographic apparatus 12 performs a second stereographic image capturing process again on the breast 22 because the biopsy region 36 may be positionally displaced by the local anesthesia in step S5.

FIG. 10 is a flowchart of an operation sequence of second and subsequent stereographic image capturing processes.

In the second stereographic image capturing process in step S6, the doctor or radiological technician determines whether the irradiated field 132 of the radiation 24b, 24c is to be restricted to the irradiated field 134 or not in step S20 shown in FIG. 10.

If in step S20 the biopsy region 36 is not largely positionally displaced by the local anesthesia and the doctor or radiological technician judges that the biopsy region 36 will be included in two radiographic images to be acquired even if the irradiated field 132 is restricted to the irradiated field 134 (step S20: YES), then the doctor or radiological technician operates the irradiated field calculation controller 124 to enable the irradiated field calculator 126 to perform its processing function.

In step S21, the irradiated field calculator 126 reads the image capturing conditions for the previous stereographic image capturing process (the first stereographic image capturing process in step S3) which have been set in the image capturing condition setting section 92.

In step S22, the irradiated field calculator 126 calculates the positions of the shield plates 70a through 70d corresponding to the restricted irradiated field 134 such that the biopsy region 36 will be located on the central axes 130b, 130c and be included in the irradiated range of the radiation 24, using the three-dimensional positions of the radiation source 26 at the two image capturing angles +θ1, −θ1, the positional information of the shield plates 70a through 70d in the previous stereographic image capturing process, and the three-dimensional position of the biopsy region 36 based on the radiographic image in the previous stereographic image capturing process, calculated in step S3, among the image capturing conditions of the previous stereographic image capturing process.

The irradiated field calculator 126 sets the calculated positions of the shield plates 70a through 70d as new image capturing conditions of the second stereographic image capturing process in step S6 in the image capturing condition setting section 92, thereby updating the setting contents of image capturing condition setting section 92.

In step S23, the mammographic apparatus 12 turns the radiation source housing unit 28 about the hinge 42 (see FIG. 1) to place the radiation source 26 in the position B (see FIG. 6).

Then, the collimator controller 98 energizes the motors 76a through 76d of the collimator 60 according to the updated image capturing conditions from the image capturing condition setting section 92. The shield plates 70a through 70d are moved to the position represented by the new image capturing conditions, thus restricting the position and area of the opening 82 to a position and area corresponding to the restricted irradiated field 134.

In step S24, the light source controller 96 energizes the light source 62 to emit illuminating light. The emitted illuminating light is reflected by the mirror 64 and passes through the opening 82 toward the breast 22. The illuminating light is applied to the compression plate 34 and the like, indicating a light irradiated field. At this time, the light irradiated field is limited to the size representing the irradiated field 134.

In step S25, after having confirmed the light irradiated field, the doctor or radiological technician turns on the exposure switch. The radiation source controller 94 now energizes the radiation source 26 placed in the position B (+θ1) according to the new image capturing conditions from the image capturing condition setting section 92.

The radiation 24b emitted from the radiation source 26 in the position B passes through the opening 82, and is applied to the breast 22. The radiation 24b then passes through the breast 22, and is detected by the solid-state detector 30 as radiation representing a first radiographic image of the breast 22. As the position and area of the opening 82 have been restricted according the new image capturing conditions, the irradiated range of the radiation 24b is restricted from the range indicated by the broken lines to the range indicated by the one-dot-and-dash lines, and hence the irradiated field is restricted from the irradiated field 132 to the irradiated field 134 which covers the biopsy region 36.

The detector controller 100 controls the solid-state detector 30 to acquire a single radiographic image from the detected radiation and to store the acquired radiographic image as the first radiographic image in the image information storage unit 102 temporarily.

Then, the mammographic apparatus 12 determines whether the second stereographic image capturing process has been completed or not in step S26.

Since a second radiographic image based on the radiation from the radiation source 26 in the position C in FIG. 7 has not been captured though the radiographic image based on the radiation from the radiation source 26 in the position B has been captured (step S26: NO), the mammographic apparatus 12 moves the radiation source 26 to the position C and captures a second radiographic image based on the radiation 24c from the radiation source 26 in the position C by carrying out steps S23 through S25 again in a similar manner to the image capturing process in the position B.

The second radiographic image is acquired and stored in the image information storage unit 102 (step S26: YES) in the position C temporarily. Thereafter, the CAD processor 104 processes the two radiographic images stored in the image information storage unit 102, and displays the processed radiographic images on the display unit 106 and the display control panel 40.

The doctor or radiological technician sees the two radiographic images displayed on the display unit 106 and/or the display control panel 40, and operates the biopsy region selector 108 to selects once again the biopsy region 36 from which a tissue is to be sampled, from the biopsy regions 36 in the displayed two radiographic images. Then, the biopsy region positional information calculator 110 calculates the three-dimensional position of the selected biopsy region 36, and displays the calculated three-dimensional position on the display unit 106 and the display control panel 40.

In step S20 in FIG. 10, if the biopsy region 36 is largely positionally displaced by the local anesthesia and the doctor or radiological technician judges that that the biopsy region 36 will possibly be not included in two radiographic images to be acquired if the irradiated field 132 is restricted to the irradiated field 134 (step S20: NO), then the doctor or radiological technician keeps the irradiated field calculator 126 disabled to its processing function. In and after step S23, the mammographic apparatus 12 performs a stereographic image capturing process under the same image capturing conditions (including the irradiated field 132) as with the stereographic image capturing process in step S3.

In step S7, the doctor or radiological technician makes an incision in the surface of the breast 22 with a surgical knife at a position where the biopsy needle 56 is to be inserted, and then inserts the biopsy needle 56 through the incision into the breast 22. At this time, the doctor or radiological technician pushes the biopsy needle 56 until the tip end of the biopsy needle 56 reaches a position immediately short of the biopsy region 36 in the breast 22.

In step S8, the mammographic apparatus 12 performs a stereographic image capturing process again in the same manner as the stereographic image capturing process in step S6, in order to confirm whether the biopsy needle 56 is inserted along a direction aligned with the biopsy region 36 or not.

If the irradiated field is to be restricted (step S20: YES) in step S8, then positional information of the shield plates 70a through 70d in the stereographic image capturing process in step S8 is calculated using the image capturing conditions of the stereographic image capturing process in step S6 and the three-dimensional position of the biopsy region 36 based on the two radiographic images acquired in the stereographic image capturing process in step S6, in steps S21, S22. In step S23 and subsequent steps, the stereographic image capturing process is carried out according to the image capturing conditions including the calculated positional information.

When the two radiographic images captured in the stereographic image capturing process in step S8 are displayed on the display unit 106 and the display control panel 40, the doctor or radiological technician operates the biopsy region selector 108 to selects once again the biopsy region 36 from which a tissue is to be sampled, from the biopsy regions 36 in the displayed two radiographic images in a similar manner to step S4. Then, the biopsy region positional information calculator 110 calculates the three-dimensional position of the selected biopsy region 36, and displays the calculated three-dimensional position on the display unit 106 and the display control panel 40 and outputs the calculated three-dimensional position to the traveled distance calculator 120.

In step S9, the traveled distance calculator 120 calculates the distance by which the biopsy needle 56 is to move with respect to the biopsy region 36, based on the three-dimensional position of the biopsy region 36, the position of the tip end of the biopsy needle 56 which has been calculated by the biopsy needle positional information calculator 114, and the positional information of the compression plate 34 which has been calculated by the compression plate positional information calculator 118, and outputs the calculated distance to the biopsy needle controller 112. The biopsy needle controller 112 can now move the sampler 58 of the biopsy needle 56 to the biopsy region 36.

In step S10, the mammographic apparatus 12 performs a stereographic image capturing process again in the same manner as the stereographic image capturing process in steps S6, S8 in order to confirm whether the position of the biopsy region 36 and the position and direction of the sampler 58 are in agreement with each other or not.

If the irradiated field is to be restricted (step S20: YES), then positional information of the shield plates 70a through 70d in the stereographic image capturing process in step S10 is calculated using the image capturing conditions of the stereographic image capturing process in step S8 and the three-dimensional position of the biopsy region 36 based on the two radiographic images acquired in the stereographic image capturing process in step S8, in steps S21, S22. In step S23 and subsequent steps, the stereographic image capturing process is carried out according to the image capturing conditions including the calculated positional information.

When the two radiographic images captured in the stereographic image capturing process in step S10 are displayed on the display unit 106 and the display control panel 40, the doctor or radiological technician can easily confirm from the displayed radiographic images whether the position of the biopsy region 36 and the position and direction of the sampler 58 are in agreement with each other or not.

In step S11, the biopsy needle 56 starts to sample a tissue from the biopsy region 36 under suction. Thereafter, the sampled tissue is inspected by an inspecting apparatus, not shown, to check, for example, if the tissue is calcified or not in step S12.

In step S13, the mammographic apparatus 12 performs a stereographic image capturing process again in the same manner as the stereographic image capturing process in steps S6, S8, S10 in order to confirm that the tissue has been sampled from the biopsy region 36.

If the irradiated field is to be restricted (step S20: YES), then positional information of the shield plates 70a through 70d in the stereographic image capturing process in step S13 is calculated using the image capturing conditions of the stereographic image capturing process in step S10 and the three-dimensional position of the biopsy region 36 based on the two radiographic images acquired in the stereographic image capturing process in step S10, in steps S21, S22. In step S23 and subsequent steps, the stereographic image capturing process is carried out according to the image capturing conditions including the calculated positional information.

When the two radiographic images captured in the stereographic image capturing process in step S13 are displayed on the display unit 106 and the display control panel 40, the doctor or radiological technician can easily confirm from the displayed radiographic images whether the tissue has been sampled from the biopsy region 36 or not.

Thereafter, the biopsy needle 56 is moved in the direction indicated by the arrow Z to remove the biopsy needle 56 from the breast 22 in step S14. The operation sequence shown in FIG. 9 is now ended.

After all the tissue has been sampled from the biopsy region 36, the position of the biopsy region 36 may not subsequently be confirmed. To provide against such a situation, a marker is inserted into the biopsy region 36 prior to step S14. Specifically, a marker made of stainless steel is inserted into the biopsy region 36 by the sampler 58 of the biopsy needle 56 in step S15. Thereafter, the mammographic apparatus 12 performs a scout image capturing process again in the same manner as the scout image capturing process in step S2 in order to confirm the inserted marker in step S16. The display unit 106 and the display control panel 40 display a single radiographic image acquired by the scout image capturing process, based on which the doctor or radiological technician can easily confirm the marker inserted in the biopsy region 36. After the marker has been confirmed, the biopsy needle 56 is removed from the breast 22 in step S14.

As described above, the mammographic apparatus 12 according to the present embodiment calculates an irradiated field (new irradiated field) in a next (or present) stereographic image capturing process based on the three-dimensional position of the biopsy region 36 which is obtained in a present (or previous) stereographic image capturing process, and performs the next stereographic image capturing process with the new irradiated field. Since the new irradiated field around the biopsy region 36 is irradiated with the radiation 24 in the next stereographic image capturing process, the radiation 24 is prevented from being applied to body regions of the examinee 20 which have nothing to do with the calculation of the three-dimensional position of the biopsy region 36, and hence the examinee 20 is prevented from being unduly exposed to the radiation 24.

Even if the breast 22 is moved or positionally or angularly changed between stereographic image capturing processes or the radiation source 26 disposed at two image capturing angles suffers angular errors, since a new irradiated field around the biopsy region 36 is irradiated with the radiation 24 in a next stereographic image capturing process, two radiographic images acquired in the next stereographic image capturing process reliably cover the biopsy region 36. Consequently, it is possible to perform a stereographic image capturing process on the biopsy region 36 and to accurately calculate the three-dimensional position of the biopsy region 36 regardless of a movement or positional or angular change of the breast 22 or angular errors of the radiation source 26.

According to the present embodiment, therefore, the examinee 20 is prevented from being unduly exposed to the radiation 24, and a stereographic image capturing process is reliably performed on the biopsy region 36 in the breast 22 to accurately calculate the three-dimensional position of the biopsy region 36.

If steps S20 through S26 are carried out in each of the stereographic image capturing processes in steps S6, S8, S10, S13, then the application of the radiation 24 to the breast 22 from the radiation source 26 at the two image capturing angles, the calculation of the three-dimensional position of the biopsy region 36 by the biopsy region positional information calculator 110, the calculation of a new irradiated field by the irradiated field calculator 126, and the changing of the present irradiated field to the new irradiated field by the collimator controller 98 are successively carried out repeatedly.

Accordingly, the present stereographic image capturing process is performed while reflecting the result (the three-dimensional position of the biopsy region 36) of the previous stereographic image capturing process, and the next stereographic image capturing process is performed while reflecting the result of the present stereographic image capturing process. As a result, even if the breast 22 is moved or positionally or angularly changed between stereographic image capturing processes or the radiation source 26 disposed at two image capturing angles suffers angular errors, the radiation source 26 can apply the radiation 24 to the breast 22 within a new irradiated field around the biopsy region 36. In other words, the radiation source 26 applies the radiation 24 to the breast 22 while at the same time tracking the biopsy region 36.

The irradiated field calculation controller 124 can selectively enables the irradiated field calculator 126 to calculate the new irradiated field or disables the irradiated field calculator 126 to stop calculating the new irradiated field. If any movement or positional or angular change of the breast 22 between stereographic image capturing processes is small (step S20: YES), then the irradiated field calculation controller 124 enables the irradiated field calculator 126 to calculate the new irradiated for thereby preventing the examinee 20 from being unduly exposed to the radiation. On the other hand, if the breast 22 is greatly moved or positionally or angularly changed between stereographic image capturing processes (step S20: NO), then the irradiated field calculation controller 124 disables the irradiated field calculator 126 to stop calculating the new irradiated field, and the radiation 24 is applied to the breast 22 in a wider irradiated field, for thereby allowing the biopsy region 36 to be reliably covered by a radiographic image.

Before the radiation source 26 applies the radiation 24 to the breast 22, the light source 62 applies illuminating light to spotlight the breast 22 to indicate an irradiated field thereon. It is thus easy to confirm whether there exists any obstacle to a stereographic image capturing process between the radiation source 26 and the breast 22, before the stereographic image capturing process is carried out.

As shown in FIGS. 6 and 7, the sizes of the irradiated fields 132, 134 remain the same at the positions B, C in the stereographic image capturing process. However, the sizes of the irradiated fields 132, 134 may be different at the positions B, C (in the left and right) in the stereographic image capturing process insofar as the biopsy region 36 is covered in the acquired radiographic images.

The doctor or radiological technician may operate the angle setting unit 122 to set a radiating angle in the image capturing condition setting section 92, and the irradiated field calculator 126 may calculate the positional information of the shield plates 70a through 70d based on the radiating angle thus set. The radiating angle set by the doctor or radiological technician should preferably be an angle selected in view of angular errors of the radiation source 26.

Although a certain preferred embodiment of the present invention has been shown and described in detail, it should be understood that various changes and modifications may be made therein without departing from the scope of the appended claims.

What is claimed is:

1. A radiographic image capturing apparatus comprising:
a radiation source configured to apply radiation to an object of a subject to be examined;
a radiation detector configured to detect the radiation that has passed through the object and configured to convert the detected radiation into a radiographic image;
a collimator configured to delimit an irradiated field of the radiation with respect to the radiation detector, the collimator being disposed between the radiation source and the object;
a biopsy region positional information calculating unit configured to calculate a three-dimensional position of a biopsy region in the object based on two radiographic images, which are acquired by the radiation detector in a stereographic image capturing process, in which the radiation source disposed at least at two angles applies the radiation to the object;
an irradiated field calculating unit configured to calculate a new irradiated field covering the biopsy region based on the calculated three-dimensional position of the biopsy region and the two angles;
a collimator control unit configured to control the collimator to change the irradiated field of the radiation in a next stereographic image capturing process to the new irradiated field; and
an irradiated field calculation control unit configured to selectively enable the irradiated field calculating unit to calculate the new irradiated field or disable the irradiated field calculating unit from calculating the new irradiated field.

2. A radiographic image capturing apparatus according to claim 1, wherein the application of the radiation to the object from the radiation source at the two angles, the calculation of the three-dimensional position of the biopsy region by the biopsy region positional information calculating unit, the calculation of the new irradiated field by the irradiated field calculating unit, and the changing of the irradiated field of the radiation to the new irradiated field by the collimator control unit are successively carried out repeatedly.

3. A radiographic image capturing apparatus according to claim 1, further comprising a light source for spotlighting the radiation detector to indicate the irradiated field thereon, before the radiation source applies the radiation to the object.

4. A radiographic image capturing apparatus according to claim 1, wherein on condition that the irradiated field calculation control unit determines that the biopsy region will possibly be included in the two radiation images to be acquired even after converting the irradiated field to the new irradiated field in the next stereographic image capturing process, then calculation of the new irradiated field by the irradiated field calculating unit is enabled, and
on condition that the irradiated field calculation control unit determines that the biopsy region will not possibly be included in the two radiation images to be acquired after converting the irradiated field to the new irradiated field in the next stereographic image capturing process, calculation of the new irradiated field by the irradiated field calculating unit is disabled.

5. A radiographic image capturing apparatus according to claim 4, wherein in the case that the calculation of the new irradiated field is enabled, the irradiated field calculating unit is configured to calculate the new irradiated field using the three-dimensional position of the biopsy region based on the radiographic image in a last stereographic image capturing process and the two angles acquired by the radiation detector in the last stereographic image capturing process.

6. A radiographic image capturing apparatus according to claim 5, wherein the irradiated field calculating unit is configured to determine a field restricted from the irradiated field, as the new irradiated field in the next stereographic image capturing process.

7. A radiographic image capturing apparatus according to claim 4, wherein in the case that the calculation of the new irradiated field is disabled, a stereographic image capturing process is carried out under the same conditions as the last stereographic image capturing process.

8. A radiographic image capturing method comprising the steps of:

performing a stereographic image capturing process by applying radiation from a radiation source disposed at least at two angles to an object of a subject to be examined, while an irradiated field of the radiation with respect to a radiation detector is being delimited by a collimator;

detecting, with the radiation detector, the radiation applied from the radiation source disposed at the two angles to acquire two radiographic images;

calculating, with a biopsy region positional information calculating unit, a three-dimensional position of a biopsy region in the object based on the two radiographic images;

calculating, with an irradiated field calculating unit, a new irradiated field covering the biopsy region based on the calculated three-dimensional position of the biopsy region and the two angles;

controlling the collimator with a collimator control unit to change the irradiated field of the radiation in a next stereographic image capturing process to the new irradiated field; and selectively enabling the irradiated field calculating unit to calculate the new irradiated field or disabling the irradiated field calculating unit from calculating the new irradiated field.

* * * * *